(12) United States Patent
Grasso

(10) Patent No.: US 11,425,514 B2
(45) Date of Patent: Aug. 23, 2022

(54) UNIVERSAL BONE CONDUCTION AND MIDDLE EAR IMPLANT

(71) Applicant: MED-EL Elektromedizinische Geraete GmbH, Innsbruck (AT)

(72) Inventor: Peter Grasso, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 17/279,035

(22) PCT Filed: Sep. 23, 2019

(86) PCT No.: PCT/US2019/052331
§ 371 (c)(1),
(2) Date: Mar. 23, 2021

(87) PCT Pub. No.: WO2020/068604
PCT Pub. Date: Apr. 2, 2020

(65) Prior Publication Data
US 2022/0053277 A1    Feb. 17, 2022

Related U.S. Application Data

(60) Provisional application No. 62/735,220, filed on Sep. 24, 2018.

(51) Int. Cl.
*H04R 25/00* (2006.01)
*A61F 2/18* (2006.01)

(52) U.S. Cl.
CPC .............. *H04R 25/606* (2013.01); *A61F 2/18* (2013.01); *H04R 25/55* (2013.01);
(Continued)

(58) Field of Classification Search
CPC ................................................ H04R 2460/13
(Continued)

(56) References Cited

U.S. PATENT DOCUMENTS

| 4,606,329 A | 8/1986 | Hough |
| 5,015,224 A | 5/1991 | Maniglia |

(Continued)

FOREIGN PATENT DOCUMENTS

| EP | 0 936 840 A1 | 8/1999 |
| WO | WO 2014/039743 A1 | 3/2014 |

OTHER PUBLICATIONS

International Searching Authority/US, International Search Report and Written Opinion of the International Searching Authority, Application No. PCT/US2019/052331, dated Dec. 3, 2019, 12 pages.

(Continued)

*Primary Examiner* — Suhan Ni
(74) *Attorney, Agent, or Firm* — Sunstein LLP

(57) ABSTRACT

A middle ear implant system includes a bone conduction transducer configured for fixed attachment to skull bone of a patient beneath the skin behind the ear, and for generating sound vibrations from an external communications signal received through the skin for coupling to the skull bone for bone conduction sound perception by the patient. A malleable ossicle connector is connected to the bone conduction transducer and a middle ear hearing structure of the patient. And one or more isolation springs are configured for placement at the fixed attachment of the bone conduction transducer to the skull bone to acoustically decouple the bone conduction transducer from the skull bone to avoid bone conduction sound perception so that sound perception from the external communications signal is solely via the middle ear sound perception from vibrations coupled to the middle ear hearing structure by the ossicle connector.

9 Claims, 7 Drawing Sheets

(52) U.S. Cl.
CPC .... *A61F 2002/183* (2013.01); *H04R 2225/67* (2013.01); *H04R 2460/13* (2013.01)

(58) Field of Classification Search
USPC .......................................... 381/151, 326, 380
See application file for complete search history.

(56) References Cited

U.S. PATENT DOCUMENTS

| | | | |
|---|---|---|---|
| 5,624,376 | A | 4/1997 | Ball et al. |
| 7,722,524 | B2 | 5/2010 | Lupin et al. |
| 9,113,277 | B2 | 8/2015 | Ball et al. |
| 10,003,898 | B1 * | 6/2018 | Bjorn .................... H04R 25/606 |
| 2008/0051623 | A1 | 2/2008 | Schneider et al. |
| 2016/0381474 | A1 * | 12/2016 | Gustafsson .......... H04R 25/606 |
| | | | 600/25 |
| 2017/0347209 | A1 * | 11/2017 | Heasman ............. H04R 25/305 |
| 2018/0262846 | A1 | 9/2018 | Perkins et al. |

OTHER PUBLICATIONS

European Patent Office, Extended European Search Report, Application No. 19864619.2, dated May 20, 2022, 10 pages.

* cited by examiner

1

UNIVERSAL BONE CONDUCTION AND MIDDLE EAR IMPLANT

This application is the national phase entry of International Patent Application No. PCT/US2019/052331 filed Sep. 23, 2019, which claims priority from U.S. Provisional Patent Application 62/735,220, filed Sep. 24, 2018, the disclosures of which is are incorporated herein by reference in their entirety.

FIELD OF THE INVENTION

The present invention relates to medical implants, and more specifically, to a novel middle ear implant system.

BACKGROUND ART

A normal ear transmits sounds as shown in FIG. 1 through the outer ear 101 to the tympanic membrane 102 which moves the ossicles of the middle ear 103 that vibrate the oval window 106 and round window 107 membranes of the cochlea 104. The cochlea 104 is a long narrow duct wound spirally about its axis for approximately two and a half turns. The cochlea 104 forms an upright spiraling cone with a center called the modiolar where the spiral ganglion cells of the cochlear nerve 105 reside. In response to received sounds transmitted by the middle ear 103, the fluid-filled cochlea 104 functions as a transducer to generate electric pulses which are transmitted by the cochlear nerve 105 to the brain.

Hearing is impaired when there are problems in the ability to transduce external sounds into meaningful action potentials along the neural substrate of the cochlea. To improve impaired hearing, auditory prostheses have been developed. For example, when the impairment is related to operation of the middle ear, a conventional hearing aid, a middle ear implant, or a bone conduction implant may be used to provide acoustic-mechanical stimulation to the auditory system in the form of amplified sound. Or when the impairment is associated with the cochlea, a cochlear implant with an implanted stimulation electrode can electrically stimulate auditory nerve tissue with small currents delivered by multiple electrode contacts distributed along the electrode.

Middle ear implants employ electromagnetic transducers to convert sounds into mechanical vibration of the middle ear 103. A coil winding is held stationary by attachment to a non-vibrating structure within the middle ear 103 and microphone signal current is delivered to the coil winding to generate an electromagnetic field. A magnet is attached to an ossicle within the middle ear 103 so that the magnetic field of the magnet interacts with the magnetic field of the coil. The magnet vibrates in response to the interaction of the magnetic fields, causing vibration of the bones of the middle ear 103. See U.S. Pat. No. 6,190,305, which is incorporated herein by reference.

U.S. Pat. No. 8,246,532 (incorporated herein by reference in its entirety) describes a type of bone conduction implant that delivers a mechanical vibration signal to the cochlea for sound perception in persons with conductive or mixed conductive/sensorineural hearing loss. An implanted bone conduction transducer is affixed beneath the skin to the temporal bone. In response to an externally generated electrical communications signal, the transducer couples a mechanical stimulation signal to the temporal bone for delivery by bone conduction to the cochlea for perception as a sound signal. A certain amount of electronic circuitry also is implanted with the transducer to provide power to the implanted device and at least some signal processing which is needed for converting the external electrical communications signal into the mechanical stimulation signal and mechanically driving the transducer.

SUMMARY OF THE INVENTION

Embodiments of the present invention include a middle ear implant system with a bone conduction transducer configured for fixed attachment to skull bone of a patient beneath the skin behind the ear, and for generating sound vibrations from an external communications signal received through the skin for coupling to the skull bone for bone conduction sound perception by the patient. A malleable ossicle connector has a proximal end connected to the bone conduction transducer and a distal end connected to a middle ear hearing structure of the patient so that vibrations of the bone conduction transducer are mechanically coupled to the middle ear hearing structure for middle ear sound perception by the patient. And one or more isolation springs are configured for placement at the fixed attachment of the bone conduction transducer to the skull bone to acoustically decouple the bone conduction transducer from the skull bone to avoid bone conduction sound perception so that sound perception from the external communications signal is solely via the middle ear sound perception from vibrations coupled to the middle ear hearing structure by the ossicle connector.

In specific embodiments, the ossicle connector may have an adjustable length between the proximal end and the distal end and/or may be made of titanium. The ossicle connector may be configured to pass through a surgically created tunnel in the skull bone and/or the ossicle connector may be configured to connect to the ossicle so as to preserve a normal hearing pathway from the tympanic membrane of the patient.

Embodiments may also include an external communications component that is attached to the outer surface of the skin and configured to generate the external communications signal. In such embodiments, the external communications component may include an external vibration magnet configured to magnetically cooperate with the bone conduction transducer to couple the external communications signal through the skin. The external communications component may include an attachment surface configured for adhesive attachment to the outer surface of the skin to fixedly secure the external communications component to the outer surface of the skin. Or there may be an implant magnet fixedly attached to the skull bone near the bone conduction transducer, and an external holding magnet that is contained within the external communications component, wherein the implant magnet and the external holding magnet are configured to magnetically cooperate to fixedly secure the external communications component on the outer surface of the skin.

DETAILED DESCRIPTION OF SPECIFIC EMBODIMENTS

Figure 1:
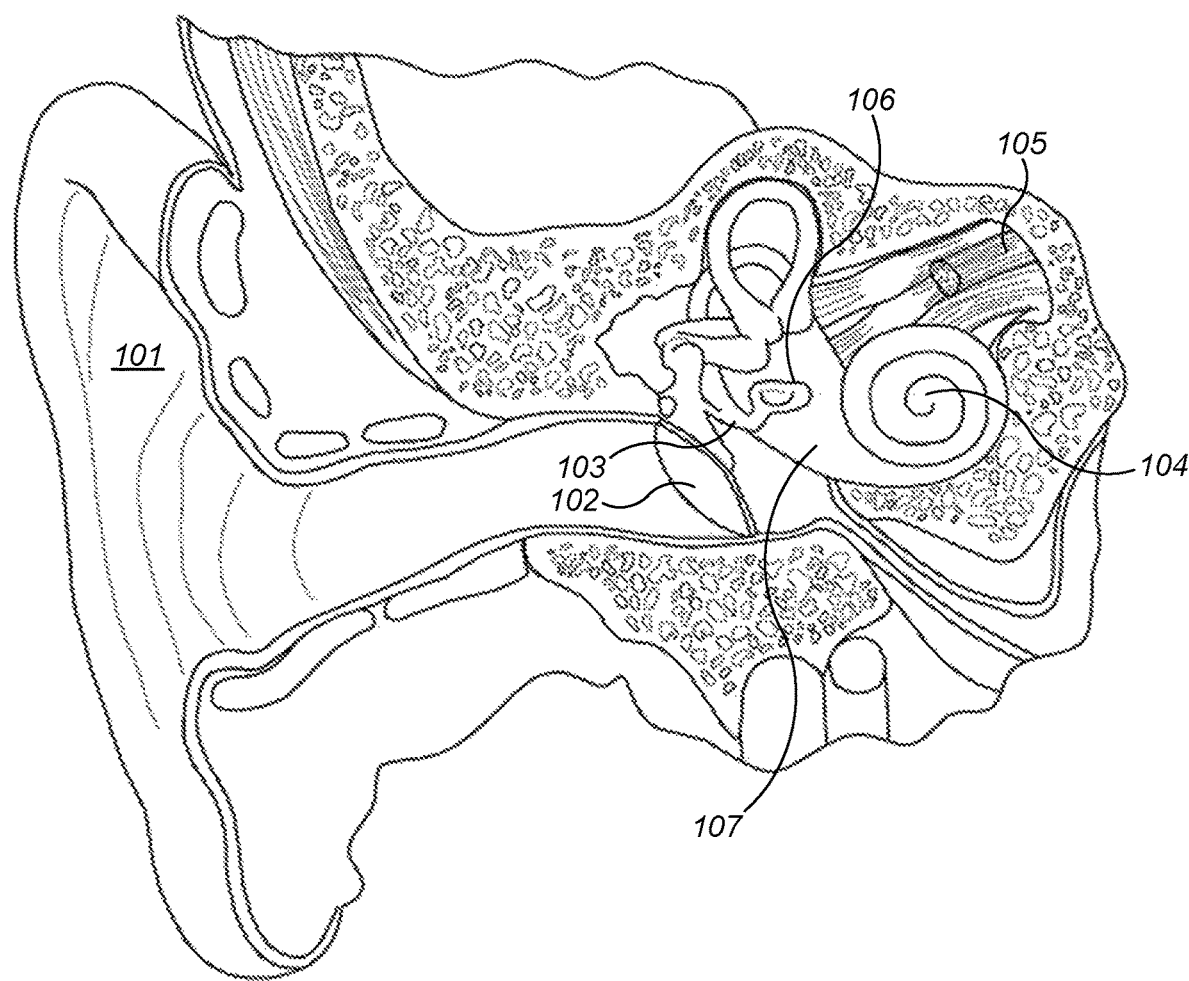
FIG. 1 shows anatomical structures of a typical human ear.
Figure 2A:
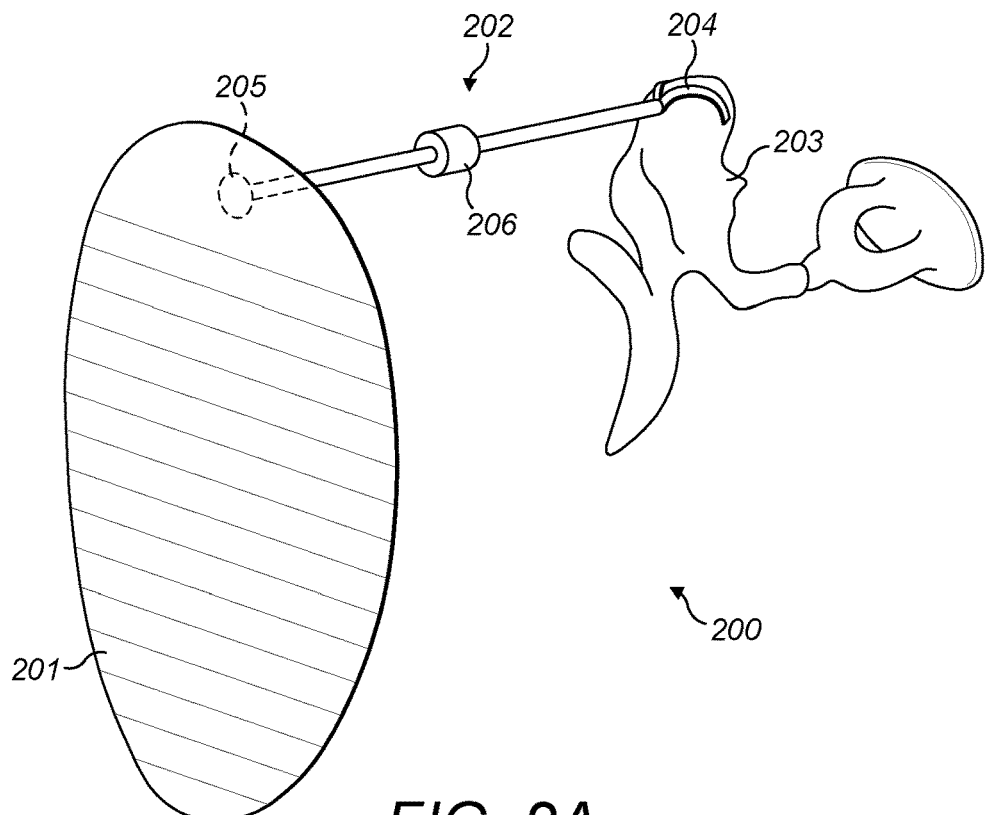
FIGS. 2A-2B show structural details of a bone conduction transducer and ossicle connector according to an embodiment of the present invention.
Figure 2B:
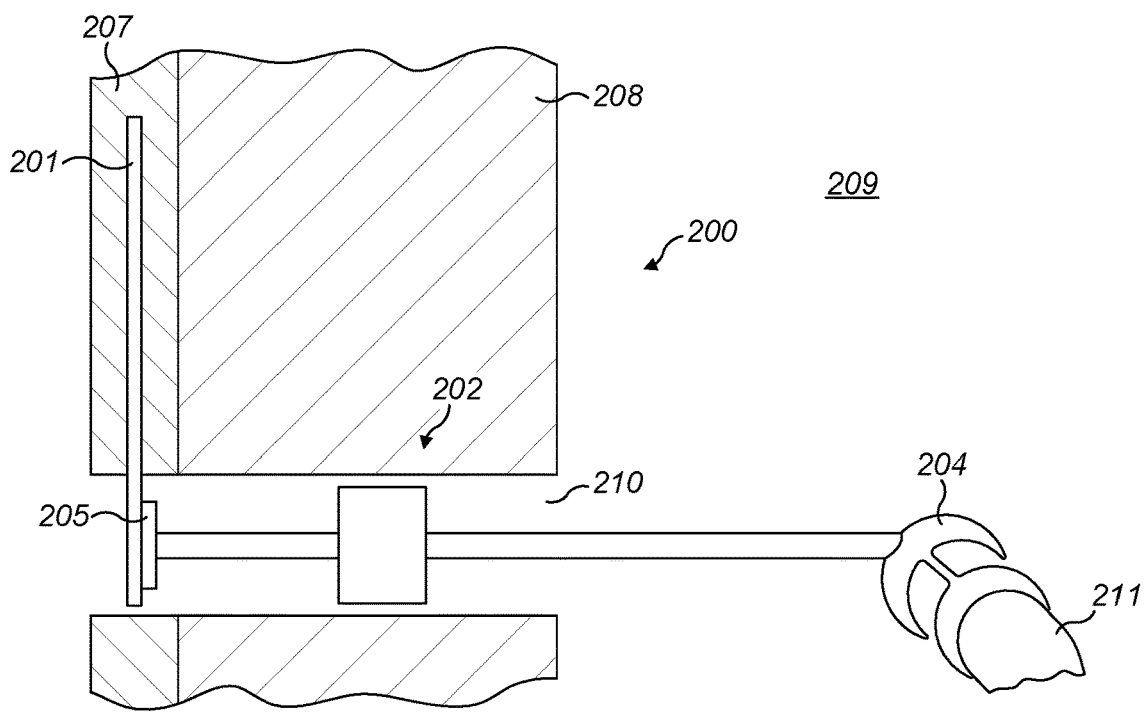

Embodiments of the present invention are directed to a novel arrangement of a middle ear implant system that includes a bone conduction transducer that is implanted within the soft tissue skin that lies over the skull bone of a patient. FIGS. 2A-2B show structural details of one specific embodiment of a middle ear implant system 200 with such a bone conduction transducer 201—in this case, in the specific form of a titanium disc-shape housing—that is configured for implantation in the skin 207 so as to be parallel to an outer surface of the skin 207 and to the skull bone 208.

A rigid ossicle connector 202 (e.g., made of titanium) has a proximal end 205 that is connected to the bone conduction transducer 201 that is embedded in the skin 207. The body of the ossicle connector 202 passes through a surgically excavated tunnel 210 in the skull bone 208 and the distal end 204 of the ossicle connector 204 connects to an ossicle 211 in the middle ear 209 of the patient so that vibrations of the bone conduction transducer 201 are mechanically coupled to the ossicle 211 for perception by the patient as sound. At the same time, an arrangement as shown also preserves a normal hearing pathway from the tympanic membrane of the patient for normal sound perception.

The ossicle connector 202 shown also includes an adjustment mechanism 206 such as a zip-connector style mechanism that allows the surgeon to adjust the length of the ossicle connector 202 when implanting the device. In addition or alternatively, the length of the ossicle connector 202 may also include one or more strain reliefs (such as one or more spring windings).

Figure 3A:
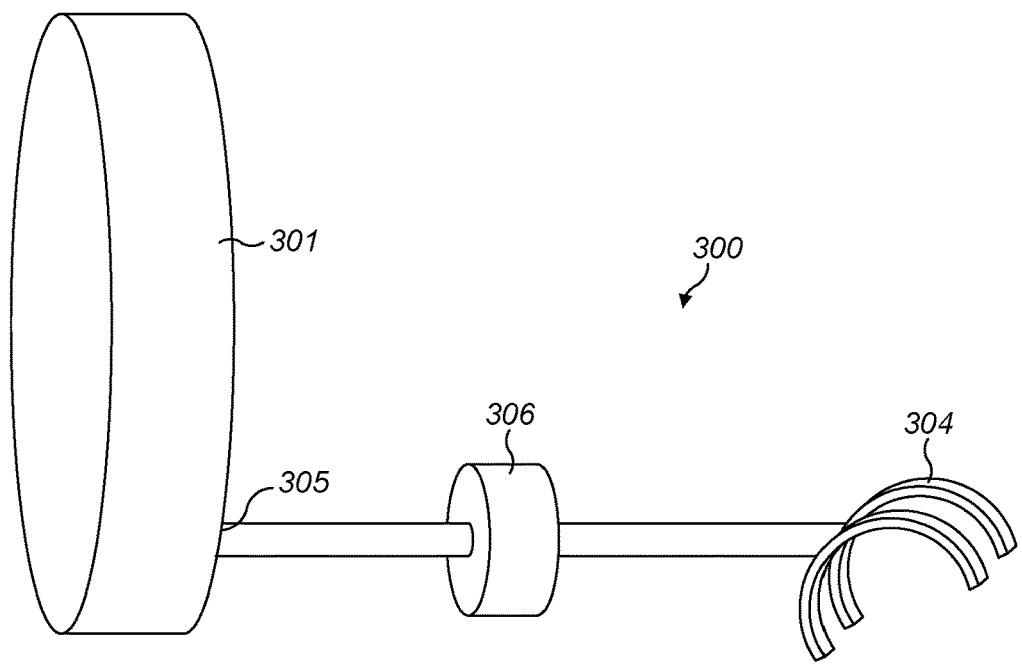
FIGS. 3A-3B show structural details of a bone conduction transducer and ossicle connector according to another embodiment of the present invention.
Figure 3B:
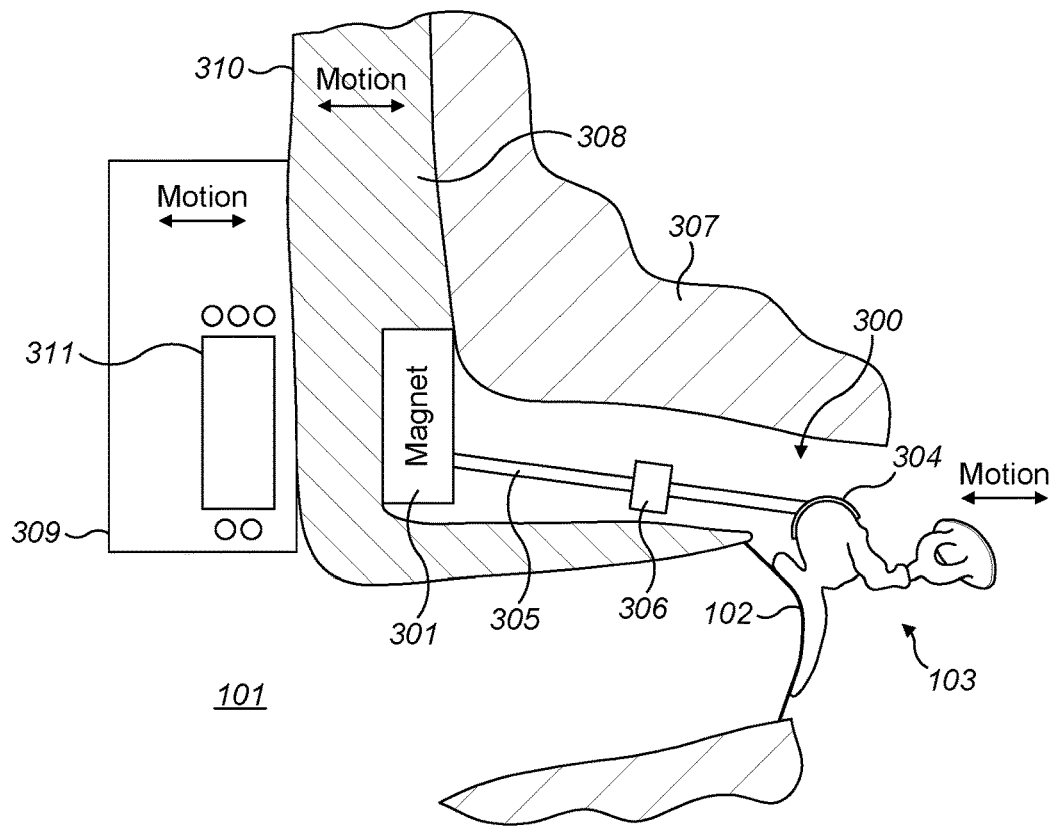

FIGS. 3A-3B show structural details of a bone conduction transducer and ossicle connector according to another embodiment of the present invention that uses an active external component 309 and wherein the bone conduction transducer 301 is a permanent magnet embedded in the skin 308 over the skull bone 307. The proximal end 305 of the ossicle connector 300 is connected to the bone conduction transducer 301 in the skin 308. The body of the ossicle connector 300 passes through a surgically excavated tunnel 310 in the skull bone 307 (via adjustment mechanism 306) and the distal end 304 of the ossicle connector 300 connects to an ossicle in the middle ear 103.

An external active vibration component 309 is attached to the outer surface 310 of the skin 308 and configured to generate the sound vibrations for the bone conduction transducer 301. Specifically, the external active vibration component 309 contains an external vibration magnet 311 (actively driven by surrounding electromagnetic drive coils controlled by an external signal processor) that magnetically cooperates with the magnetic bone conduction transducer 301 to couple the sound vibrations through the skin 308. The external active vibration component 309 is fixedly attached to the outer surface 310 of the skin 308 via any known attachment mechanism such as by an attachment surface configured for adhesive attachment to the outer surface of the skin. Or there may be a separate implant magnet fixedly attached to the skull bone 307, and a separate external holding magnet that is contained within the external active vibration component 309, wherein the implant magnet and the external holding magnet magnetically cooperate to fixedly secure the external active vibration component 309 on the outer surface 310 of the skin 308.

Figure 4A:
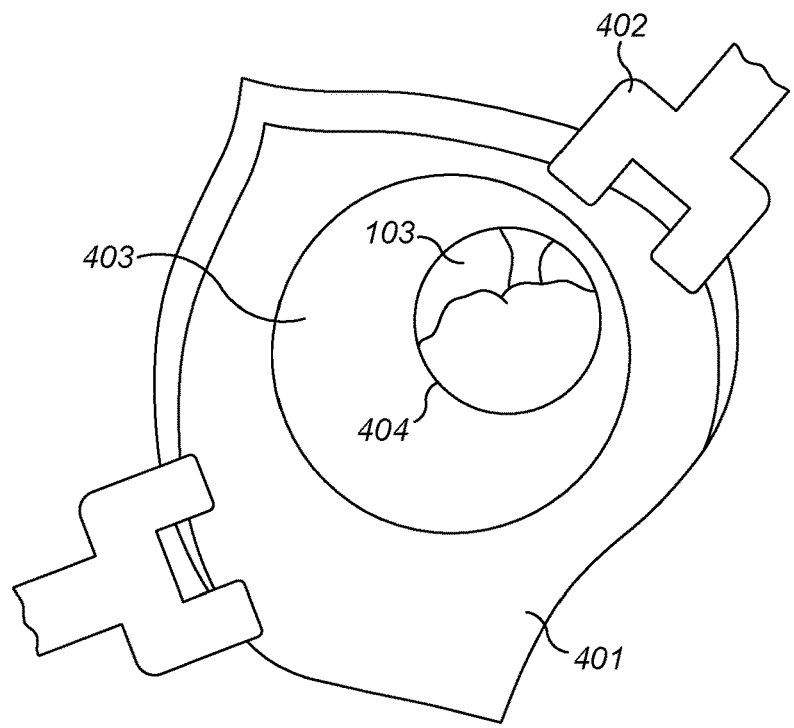
FIGS. 4A-4C show a typical surgical implantation process of a device according to an embodiment of the present invention.
Figure 4B:
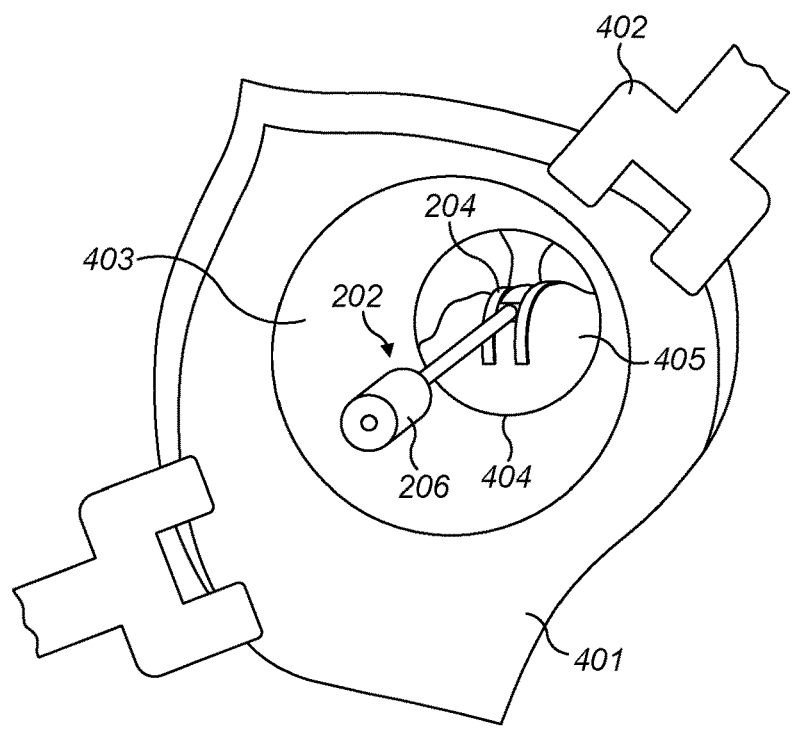
Figure 4C:
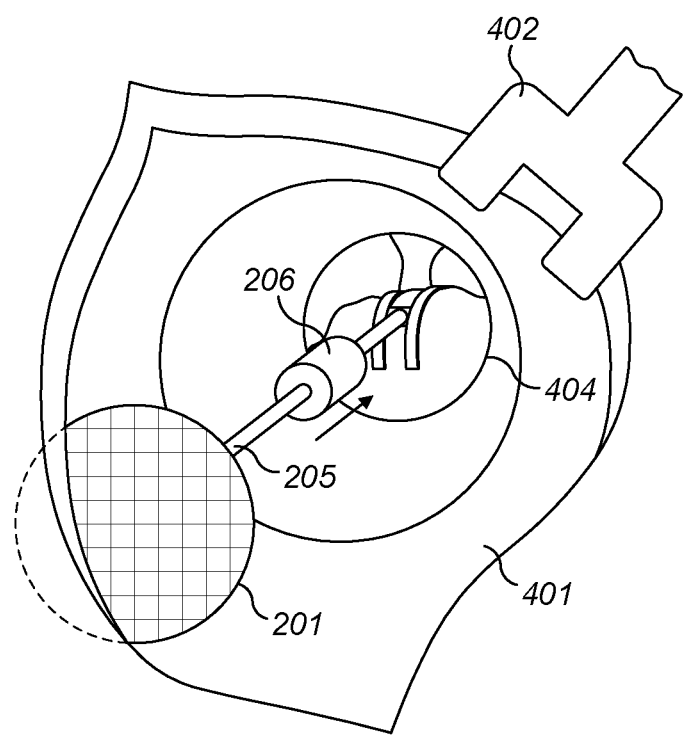

FIGS. 4A-4C show a typical surgical implantation process of a device according to an embodiment of the present invention. First, as shown in FIG. 4A, the surgeon makes an incision through the skin behind the ear 401 and uses surgical retractors 402 to expose the underlying skull bone 403. The surgeon then excavates (e.g., possibly using a robotic drill) an access tunnel 404 into the middle ear 103. The distal end 204 of the ossicle connector 202 is then connected to one of the exposed ossicles 405 (e.g., incus short process) leaving the female portion of the adjustment mechanism 206 protruding outside the access tunnel 404, FIG. 4B. The surgeon then fits the male portion of the adjustment mechanism 206 in with the proximal end 205 of the ossicle connector 202 connected to the bone conduction transducer 201 that is slid into position in the skin 401, FIG. 4C, and the incision is closed.

Figure 5A:
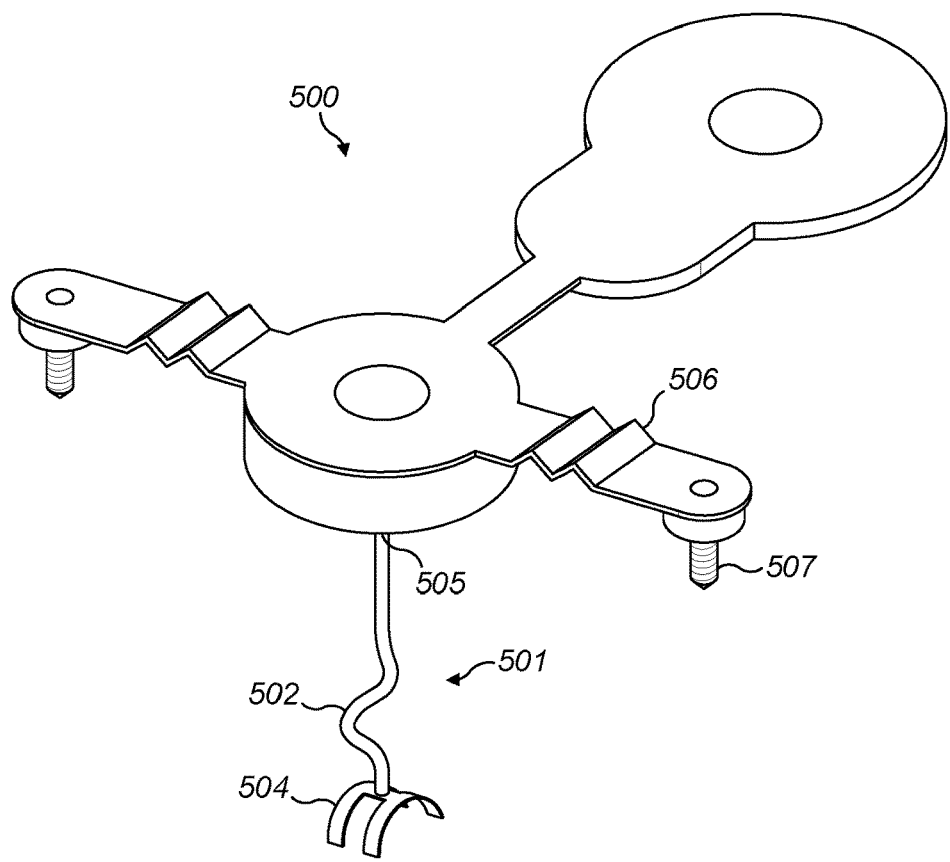
FIGS. 5A-5B show structural details of an ossicle connector attached to a bone conduction transducer according to another embodiment of the present invention.
Figure 5B:
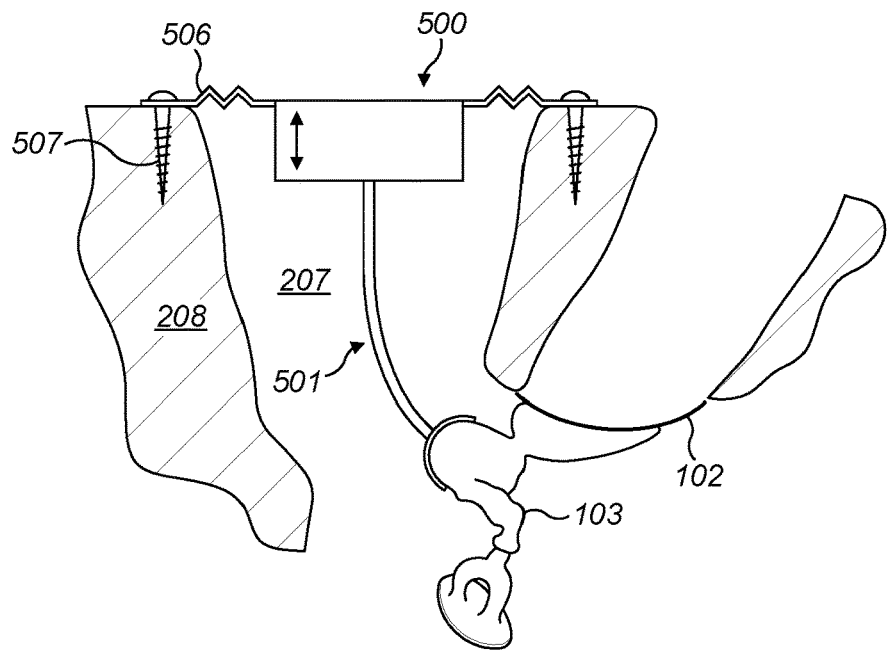

FIGS. 5A-5B show structural details of an ossicle connector 501 with a proximal end 505 attached to a bone conduction transducer 500 (e.g., Med-El's BoneBridge device) according to another embodiment of the present invention. A distal end 504 of the ossicle connector 501 connects to an ossicle in the middle ear 103. The ossicle connector 501 may include a stress relief loop 502 somewhere along its length, and may be made of titanium, gold, or other stiff biocompatible material. The bone conduction transducer 500 is connected to the adjacent skull bone 208 by flexible connecting wings 506 and bone screws 507. This allows the vibrations of the bone conduction transducer 500 (e.g., responsive to communication signals from an external signal processor device, not shown) to be coupled by the ossicle connector 501 through the skin 207 in a mastoidectomy to the connected ossicle in the middle ear 103. At the same time, the separate natural acoustic hearing pathway via the tympanic membrane 102 is preserved.

Figure 6:
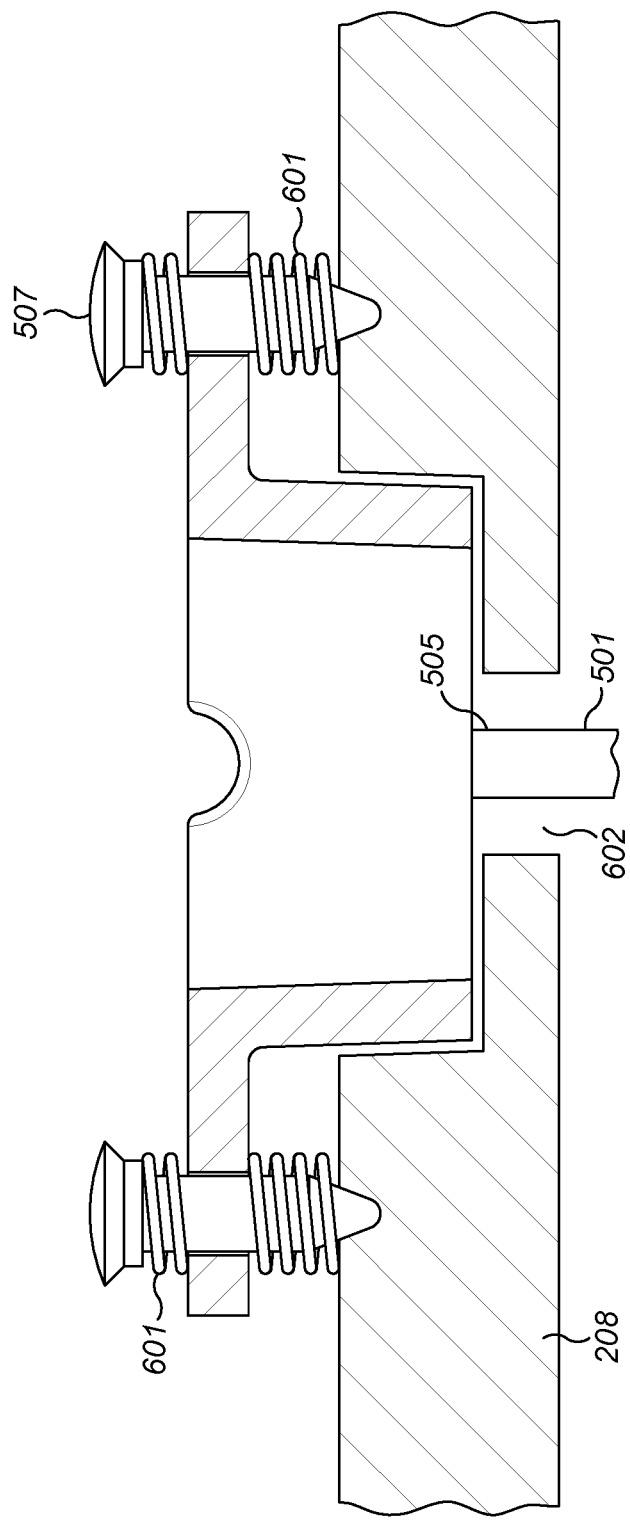
FIG. 6 shows a side cross-sectional view of a further embodiment of the invention using a bone conduction transducer that is vibrationally isolated from the connected bone.

FIG. 6 shows a side cross-sectional view of a further embodiment of the invention using a bone conduction transducer 500 such as the one in FIG. 5, but which is vibrationally isolated from the connected skull bone 208 by isolation springs 601. The isolation springs 601 can be made of silicone and are structurally separate from the conventional bone conduction transducer 500. Because the vibrations from the bone conduction transducer 500 are acoustically uncoupled from the skull bone 208 that the bone conduction transducer 500 is attached to, their sole path is via the ossicle connector 501 located in a surgically excavated tunnel 602 in the skull bone 208 below the bone conduction transducer 500 and the connected ossicle at the distal end. Specific such arrangements may be most useful at lower sound frequencies, for example, below 1000 Hz. And it may be useful to provide the isolation springs 601 as part of a surgical kit of multiple sets of springs with different elastic and acoustic properties for the surgeon to select the optimal specific set before or doing implantation. Of course, the distal end of the ossicle connector 501 in such applications may specifically be connected to other anatomical hearing structures than an ossicle in the middle ear, for example, the round window membrane, the oval window membrane, etc.

Such a modular system of a conventional bone conduction transducer 500, ossicle connector 501, and optional isolation springs 601 can usefully cover the entire range of conductive hearing loss and partial sensoneural hearing loss. By using the isolation springs 601 together with an ossicle connector 501, the arrangement acts as a middle ear implant (but with greater power from the bone conduction transducer 500 than with an FMT implanted in the middle ear). Without the ossicle connector 501 and isolation springs 601, the arrangement acts as a conventional bone conduction hearing implant system.

Although various exemplary embodiments of the invention have been disclosed, it should be apparent to those skilled in the art that various changes and modifications can be made which will achieve some of the advantages of the invention without departing from the true scope of the invention.

What is claimed is:

1. A middle ear implant system comprising:
   a bone conduction transducer configured for:
   i. fixed attachment to skull bone of a patient beneath the skin behind the ear, and
   ii. generating sound vibrations from an external communications signal received through the skin for coupling to the skull bone for bone conduction sound perception by the patient;
   a malleable ossicle connector having a proximal end connected to the bone conduction transducer and a distal end connected to a middle ear hearing structure of the patient so that vibrations of the bone conduction transducer are mechanically coupled to the middle ear hearing structure for middle ear sound perception by the patient; and
   one or more isolation springs configured for placement at the fixed attachment of the bone conduction transducer to the skull bone to acoustically decouple the bone conduction transducer from the skull bone to avoid bone conduction sound perception so that sound perception from the external communications signal is solely via the middle ear sound perception from vibrations coupled to the middle ear hearing structure by the ossicle connector.

2. The system according to claim 1, wherein the ossicle connector has an adjustable length between the proximal end and the distal end.

3. The system according to claim 1, wherein the ossicle connector is made of titanium.

4. The system according to claim 1, further comprising:
   an external communications component configured for attachment to the outer surface of the skin and generation of the external communications signal.

5. The system according to claim 4, wherein the external communications component includes an external vibration magnet configured to magnetically cooperate with the bone conduction transducer to couple the external communications signal through the skin.

6. The system according to claim 4, wherein the external communications component includes an attachment surface configured for adhesive attachment to the outer surface of the skin to fixedly secure the external communications component to the outer surface of the skin.

7. The system according to claim 4, further comprising:
   an implant magnet fixedly attached to the skull bone near the bone conduction transducer; and
   an external holding magnet contained within the external communications component, wherein the implant magnet and the external holding magnet are configured to magnetically cooperate to fixedly secure the external communications component on the outer surface of the skin.

8. The system of claim 1, wherein the ossicle connector is configured to pass through a surgically created tunnel in the skull bone.

9. The system according to claim 1, wherein the distal end of the ossicle connector is configured to connect to the ossicle so as to preserve a normal hearing pathway from the tympanic membrane of the patient.

* * * * *